(12) United States Patent
Fernandes et al.

(10) Patent No.: US 7,727,199 B2
(45) Date of Patent: Jun. 1, 2010

(54) METHODS AND DEVICES TO DELIVER INJECTED AGENTS TO AN ANEURYSM SITE

(75) Inventors: Brian Fernandes, Roseville, MN (US); Jack Chu, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 358 days.

(21) Appl. No.: 11/276,517

(22) Filed: Mar. 3, 2006

(65) Prior Publication Data

US 2006/0135942 A1 Jun. 22, 2006

Related U.S. Application Data

(63) Continuation-in-part of application No. 10/977,545, filed on Oct. 28, 2004, now abandoned.

(51) Int. Cl.
*A61M 5/178* (2006.01)
(52) U.S. Cl. .................... 604/164.09; 623/1.11
(58) Field of Classification Search ........ 604/264, 604/158, 163, 164.09; 623/1.13, 1.11, 1.42
See application file for complete search history.

(56) References Cited

U.S. PATENT DOCUMENTS

| | | | |
|---|---|---|---|
| 5,704,352 A | 1/1998 | Tremblay et al. | |
| 5,795,331 A * | 8/1998 | Cragg et al. | 604/103.01 |
| 6,052,613 A | 4/2000 | Takaki | |
| 6,129,756 A * | 10/2000 | Kugler et al. | 623/1.27 |
| 6,632,196 B1 | 10/2003 | Houser | |
| 2005/0187482 A1* | 8/2005 | O'Brien et al. | 600/486 |

FOREIGN PATENT DOCUMENTS

WO WO 2004/009082 1/2004

OTHER PUBLICATIONS

Matsuda, Takehisa, "Recent Progress of Vascular Graft Engineering in Japan" Artificial Organs, vol. 28, Issue 1, p. 64—Jan. 2004.
Tassiopoulos, Apostolos K., "Angiogenic Mechanisms of Endothelialization of Cardiovascular Implants: A Review of Recent Investigative Strategies" J. Biomater. Sci. Polymer Edn. vol. 11, No. 11, pp. 1275-1284 (2000).

* cited by examiner

*Primary Examiner*—Kevin C Sirmons
*Assistant Examiner*—Deanna K Hall
(74) *Attorney, Agent, or Firm*—Brian Novak

(57) ABSTRACT

Method and devices to administer a bioactive material within a vessel while maintaining nearly-constant pressure within the vessel are disclosed. In one embodiment the methods and devices include a multi-lumen catheter to administer bioactive materials and simultaneously drain or evacuate excess fluid or bio-inactive materials at an aneurysm site within a vessel.

8 Claims, 5 Drawing Sheets

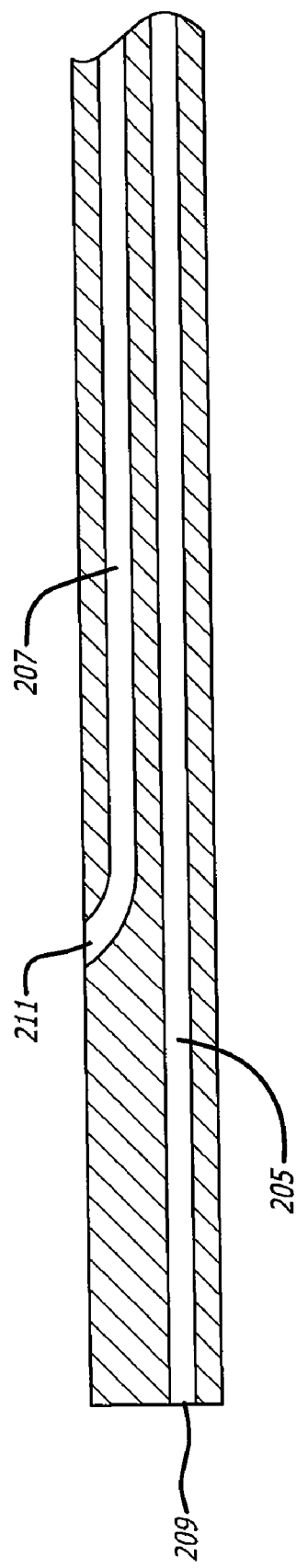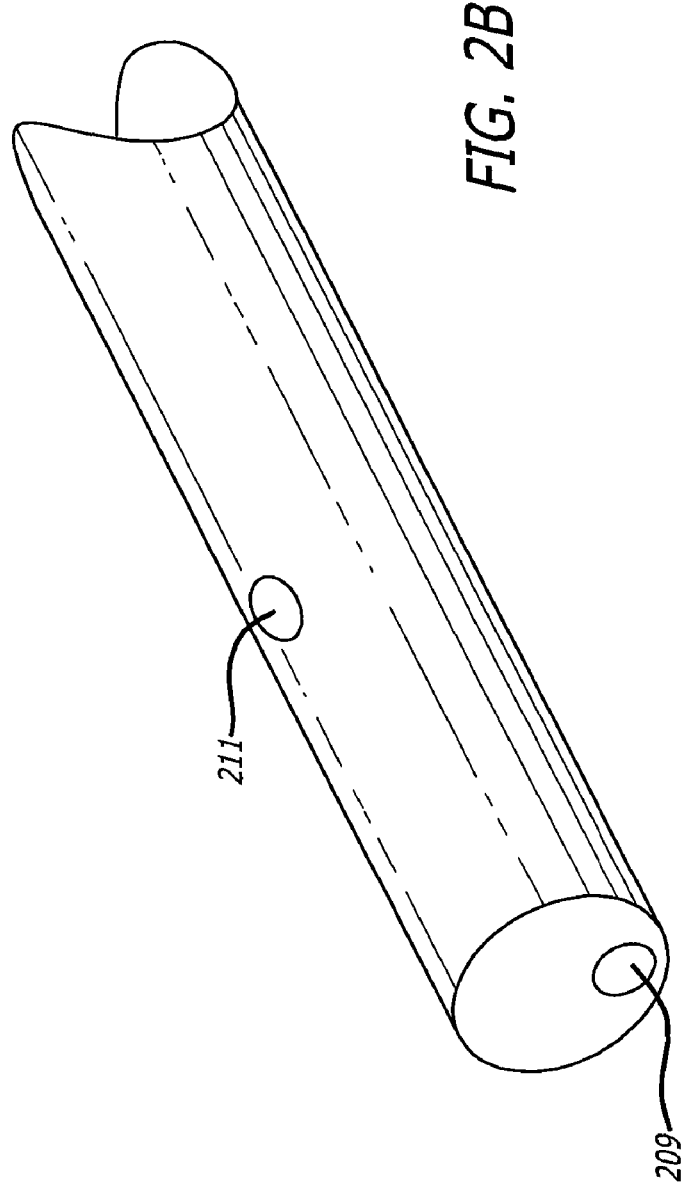

METHODS AND DEVICES TO DELIVER INJECTED AGENTS TO AN ANEURYSM SITE

CROSS REFERENCE TO RELATED APPLICATIONS

The present application is a continuation-in-part of U.S. patent application Ser. No. 10/977,545 filed Oct. 28, 2004, now abandoned which is herein incorporated by reference in its entirety.

FIELD OF THE INVENTION

Method and devices to administer a bioactive material within a vessel while maintaining nearly-constant pressure within the vessel are disclosed. In one embodiment the methods and devices are used to administer bioactive materials at an aneurysm site within a vessel. In another embodiment, bioactive materials such as autologous platelet gel compositions are administered within a vessel while maintaining approximately constant pressure in and around the administration site.

BACKGROUND OF THE INVENTION

Aneurysms arise when a thinning, weakening section of an artery wall balloons out and are often treated when the aneurysm diameter is more than 150% of the artery's normal diameter. Aneurysms are estimated to cause approximately 32,000 deaths each year in the United States. Additionally, aneurysm deaths are suspected of being underreported because sudden unexplained deaths, about 450,000 in the United States alone, are often simply misdiagnosed as heart attacks or strokes while many of them may be due to aneurysms.

The most common and deadly form of aneurysms occur in the aorta, the large blood vessel stretching from the heart to the lower abdomen. Aortic aneurysms are detected by standard ultrasound, computerized tomography (CT) and magnetic resonance imaging (MRI) scans, and the increased use of these scanning techniques for other diseases has produced an estimated 200% increase in the diagnosis of intact aortic aneurysms. A normal aorta is between 1.6 to 2.8 centimeters wide; if an area reaches as wide as 5.5 centimeters, the risk of rupture increases such that surgery is recommended.

U.S. surgeons treat approximately 50,000 abdominal aortic aneurysms each year, typically by replacing and/or bypassing the abnormal section of vessel with a plastic or fabric graft in an open surgical procedure. A less-invasive procedure that has more recently been used is the placement of a stent graft across the aneurysm site. Stent grafts are tubular devices that span the aneurysm to provide support without replacing a section of the vessel. The stent graft, when placed within the artery at the aneurysm site, acts as a barrier between blood flow and the weakened wall of the artery, thereby decreasing pressure on the damaged portion of the artery. This less invasive approach to treat aneurysms decreases the morbidity seen with conventional aneurysm repair. Additionally, patients whose multiple medical comorbidities make them excessively high risk for conventional aneurysm repair are candidates for stent grafting. Stent grafts have also emerged as a new treatment for a related condition, acute blunt aortic injury, where trauma causes damage to the artery.

While stent grafting represents an improvement over previously-used vessel replacement techniques, there are still risks associated with the procedure. One of these risks is migration of the stent graft due to hemodynamic forces within the artery. Graft migrations lead to endoleaks, a leaking of blood into the aneurysm sac between the outer surface of the graft and the inner lumen of the blood vessel. Graft migration and resulting endoleaks are especially possible in curved portions of vessels where asymmetrical hemodynamic forces in the area can place uneven forces on the stent graft. Additionally, the asymmetrical hemodynamic forces can cause remodeling of the aneurysm sac which leads to increased risk of aneurysm rupture and increased endoleaks.

Based on the foregoing, one goal of treating aneurysms is to provide a stent graft that does not migrate. In an attempt to achieve this goal, stent grafts with stainless steel anchoring barbs that engage the vessel wall have been developed. Additionally, endostaples that fix the graft more readily to the vessel wall have been developed. While these physical anchoring devices have proven to be effective in some patients, they have not sufficiently ameliorated the graft migration and endoleak problems associated with current stent-grafting methods and devices in all cases.

An additional way to reduce the risk of stent graft migration is to administer to the treatment site, either before, during or relatively soon after stent graft implantation a cell growth promoting factor. This administration can be beneficial because, normally, the endothelial cells that make up the portion of the vessel to be treated are quiescent at the time of stent graft implantation and do not multiply. As a result, the stent graft rests against a quiescent endothelial cell layer. If cell growth promoting compositions are administered immediately before, during or relatively soon after stent graft deployment, the normally quiescent endothelial cells lining the vessel wall, and in intimate contact with the stent graft, will be stimulated to proliferate. The same will occur with smooth muscle cells and fibroblasts found within the vessel wall. As these cells proliferate they can grow into and around the stent graft lining such that portions of the stent graft becomes part of the vessel lumen rather than merely pressing against its surface. This endothelialization helps to prevent stent graft migration. In addition to cell growth promoting factors, it can be beneficial to administer a number of other bioactive materials, such as, without limitation, anti-inflammatory agents and/or anti-coagulant compounds.

While it can be beneficial to administer a bioactive material in an area to be implanted with a stent graft. This administration can also be problematic, however, because an increase in volume and internal pressure near an aneurysm site caused by the administration of an exogenous substance can increase the likelihood of aneurysm rupture. Therefore, a need exists for methods and devices that can administer a bioactive material to an aneurysm site while maintaining nearly-constant pressure in the area. Such methods and devices would allow for the introduction of beneficial bioactive materials without increasing the likelihood of aneurysm rupture.

SUMMARY OF THE INVENTION

The present invention provides methods and devices that can be used to administer bioactive materials within a vessel while maintaining nearly-constant pressure in the area. In one embodiment of the methods and devices, bioactive materials are administered at an aneurysm site while maintaining nearly-constant pressure. Methods and devices according to the present invention maintain nearly-constant pressure by providing injection catheters with at least one injection lumen and at least one exit lumen. As a bioactive material is administered within a vessel through the one or more injection lumens, displaced blood or other fluids in the area that would normally contribute to an increase in internal pressure at the administration site, instead leave the site through an exit port and lumen. Thus, nearly-constant pressure at the administration site can be maintained despite the addition of bioactive materials within the confined space.

In one embodiment of injection catheters, the injection catheter comprises a proximal end, a distal end, at least one injection (delivery) lumen and at least one exit (evacuation or drain) lumen wherein the injection lumen comprises an injection (delivery) port through which bioactive material(s) can be delivered to a treatment site and wherein the exit lumen comprises an exit (evacuation or drain) port through which fluids that would otherwise contribute to an increased volume and pressure in the area caused by the injection of bioactive materials exits the area of (is removed from) the treatment site through the exit port and exit lumen.

In another embodiment of injection catheters, the injection catheter comprises a sensor. In another embodiment, the sensor is a pressure sensor.

In another embodiment of injection catheters, the injection catheter is part of a system comprising a delivery catheter and a stent or stent graft wherein the delivery catheter comprises a retractable sheath and an injection catheter and wherein when the stent or stent graft is loaded into the delivery catheter, the injection catheter is between the retractable sheath and the stent or stent graft.

In another embodiment of injection catheters, the injection catheter is part of a system comprising a delivery catheter wherein the delivery catheter houses an injection catheter and a stent or stent graft and wherein the injection ports and the exit ports of the injection catheter are flush with the outer surface of the delivery catheter.

In another embodiment of injection catheters, along the length of the injection catheter, the exit ports are proximal to the injection ports. In another embodiment, the injection ports are proximal to the exit ports.

In another embodiment of injection catheters, the injection catheter comprises two injection lumens and two injection ports at the distal ends of the two injection lumens and two exit lumens and two exit ports at the distal ends of the exit lumens.

In another embodiment of injection catheters, along the length of the injection catheter, the exit ports are proximal to the injection ports. In another embodiment of injection catheters, along the length of the injection catheter, the injection ports are proximal to the exit ports. In another embodiment of injection catheters, along the length of the injection catheter, the injection ports and the exit ports are interspersed.

In another embodiment of injection catheters, the injection catheter comprises a guide wire lumen.

Embodiments according to the present invention may also include methods. In one embodiment the method comprises delivering a bioactive material to a treatment site comprising maintaining nearly-constant pressure at the treatment site by using an injection catheter comprising a proximal end, a distal end, at least one injection lumen and at least one exit lumen wherein the injection lumen comprises an injection port through which bioactive material(s) can be delivered to the treatment site and wherein the exit lumen comprises an exit port through which fluids that would otherwise contribute to an increased volume and pressure in the area caused by the injection of the bioactive materials exits the area of the treatment site through the exit port and exit lumen.

In another embodiment of the methods, the injection catheter comprises a sensor. In another embodiment of the methods, the sensor is a pressure sensor.

In another embodiment of the methods, the injection catheter is part of a system comprising a delivery catheter and a stent or stent graft wherein the delivery catheter comprises a retractable sheath and an injection catheter and wherein when the stent or stent graft is loaded into the delivery catheter, the injection catheter is between the retractable sheath and the stent or stent graft.

In another embodiment of the methods, along the length of the injection catheter, the exit ports are proximal to the injection ports. In another embodiment of the methods, along the length of the injection catheter, the injection ports are proximal to the exit ports. In another embodiment of the methods of the present invention, along the length of the injection catheter, the exit ports and the injection ports are interspersed.

In another embodiment of the methods, the fluid may also comprise solids that are small enough to pass through the exit ports and exit lumens. In another embodiment of the methods, the fluid is blood. In another embodiment of the methods, the fluid is predominantly blood but may also include said administered bioactive material(s).

In another embodiment of the methods, the treatment site is an aneurysm site. In another embodiment of the methods, the treatment site is an aneurysm sac. In another embodiment of the methods, the treatment site is an abdominal aneurysm sac.

BRIEF DESCRIPTION OF THE FIGURES

FIGS. 2A and 2B depict cross sectional and perspective views of an injection catheter according to the present invention.

DETAILED DESCRIPTION

Figure 1:
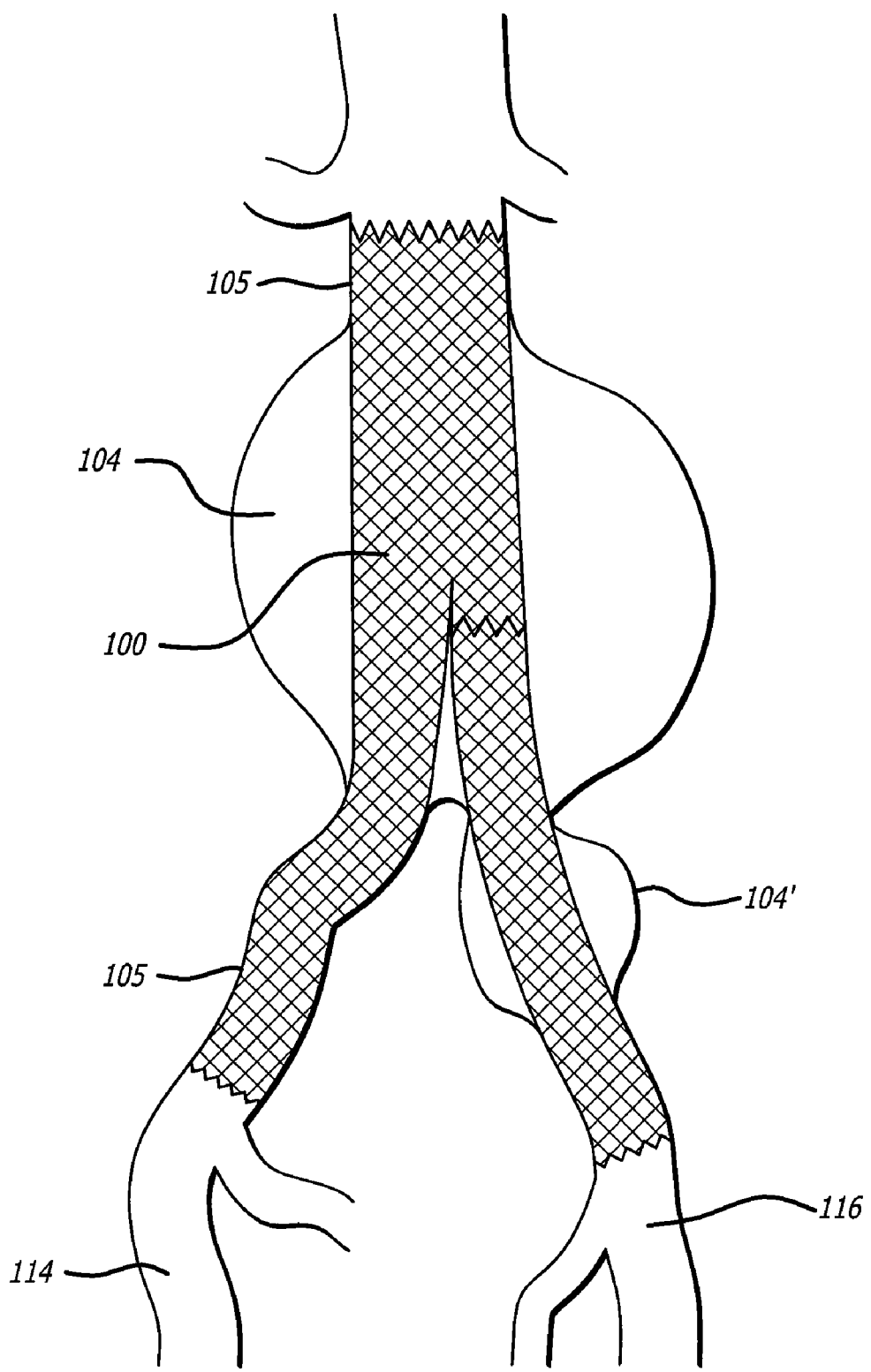
FIG. 1 depicts a fully deployed stent graft with an exterior metal scaffolding.

Prior to setting forth particular embodiments of the present invention, it may be helpful to define certain terms that will be used hereinafter:

Animal: As used herein "animal" shall include all mammals, fish, reptiles and birds.

Biocompatible: As used herein "biocompatible" shall mean any material that does not cause injury or death to the animal or induce an adverse reaction in an animal when placed in intimate contact with the animal's tissues. Adverse reactions include, without limitation, inflammation, infection, fibrotic tissue formation, cell death, embolizations, and/or thrombosis.

Bioactive material(s): As used herein "bioactive material(s)" shall include any compound or composition that creates a physiological and/or biological effect in an animal. Non-limiting examples of bioactive materials include small molecules, peptides, proteins, hormones, DNA or RNA fragments, genes, cells, genetically-modified cells, cell growth promoting compositions, matrix metalloproteinase inhibitors autologous platelet gel, other natural and synthetic gels, such as, without limitation, alginates, collagens, and hyaluronic acid, polyethylene oxide, polyethylene glycol, and polyesters, as well as combinations of these bioactive materials, including, without limitation, cell/gel combinations, protein/gel combinations, and gene/gel combinations.

Cell Growth Promoting Compositions: As used herein "cell growth promoting factors" or "cell growth promoting compositions" shall include any bioactive material having a growth promoting effect on vascular cells. Non-limiting examples of cell growth promoting compositions include vascular endothelial growth factor (VEGF), platelet-derived growth factor (PDGF), plated-derived epidermal growth factor (PDEGF), fibroblast growth factors (FGFs), transforming growth factor-beta (TGF-β), platelet-derived angiogenesis growth factor (PDAF) and autologous platelet gel (APG) including platelet rich plasma (PRP), platelet poor plasma (PPP) and thrombin.

Endoleak: As used herein "endoleak" refers to the presence of blood flow between the end of a stent graft and the vessel wall, and into the aneurysmal sac (Type I), when all such blood flow should be contained within the stent graft lumen.

Heparin Binding Growth Factor Family: As used herein "heparin binding growth factor family shall include factors binding heparin and having a positive growth effect on vascular cells. Exemplary, non limiting examples include fibroblast growth factor 1 (FGF-1), fibroblast growth factor 2 (FGF-2) and insulin-like growth factor.

Migration: As used herein "migration" refers to displacement of the stent graft from its original implanted location which may or may not be associated with a complication, such as, endoleak.

Treatment Site and Administration Site: As used herein the phrases "treatment site" and "administration site" shall mean a portion of a vessel having a stent or stent graft positioned in its vicinity. A treatment site can be, without limitation, an aneurysm site, an acute traumatic aortic injury site or a site of other vascular-associated pathology requiring stenting or stent grafting.

Vascular Growth Factor: As used herein "vascular growth factor" shall include factors having a positive effect on growth of vascular cells. Exemplary, non limiting examples include vascular endothelial growth factor A (VEGF-A), vascular endothelial growth factor B (VEGF-B), vascular endothelial growth factor C (VEGF-C), vascular endothelial growth factor D (VEGF-D) and placental growth factor.

Nearly-Constant Pressure: As used herein "nearly-constant pressure" shall include keeping the amount of pressure within an animal or patient's vascular system within the range of pressures found within said vascular system during normal physiological processes.

Embodiments provide methods and devices to administer a bioactive material at a treatment site while maintaining nearly-constant pressure at the treatment site. In one embodiment the methods and devices can be useful for preventing implantable medical device post-implantation migration and endoleak by providing for the administration of an endothelialization factor either before, during or relatively soon after the implantation of a stent or stent graft. Administered bioactive materials can also include, without limitation, anti-inflammatory and/or anti-coagulant compounds.

As discussed above, an aneurysm is a swelling, or an expansion of a blood vessel lumen at a defined point that is generally associated with a vessel wall defect. Aneurysms are often a multi-factorial asymptomatic vessel disease that if left unchecked may result in spontaneous rupture, often with fatal consequences. Previous methods to treat aneurysms involved highly invasive surgical procedures where the affected vessel region was removed and replaced or bypassed in situ with a synthetic graft that was sutured into place. This procedure, however, was extremely risky and generally only employed in otherwise healthy vigorous patients who were expected to survive the associated surgical trauma. Elderly and more feeble patients generally were not candidates for these aneurysmal surgeries and often remained untreated.

In order to overcome the risks associated with invasive aneurysmal surgeries, stent grafts were developed. Stent grafts can be deployed using minimally invasive procedures. Essentially, a catheter having a stent graft compressed and fitted into the catheter's distal tip is advanced through an artery to the aneurysmal site. The stent graft is then deployed within the vessel lumen juxtaposed to the weakened vessel wall forming an inner liner that insulates the aneurysm from the body's hemodynamic forces thereby reducing, or eliminating, the possibility of rupture. The size and shape of the stent graft is matched to a site's lumen diameter and aneurysm length. Moreover, bifurcated stent grafts are commonly used to treat abdominal aortic aneurysms that are located near the iliac branch.

FIG. 1 depicts the placement of a stent graft 100 where the iliac arteries 114 and 116 diverge from the iliac branch. As represented in FIG. 1, stent grafts 100 generally comprise a metal scaffolding surrounding a biocompatible covering such as Dacron® (E.I. du Pont de Nemours & Company, Wilmington, Del.) or a fabric-like material woven from a variety of biocompatible polymer fibers. Stent grafts can also comprise extruded sheaths and coverings. The scaffolding can be on the luminal wall-contacting surface of the stent graft where it directly contacts the vessel lumen. The sheath material is stitched, glued or molded to the scaffold. In other embodiments, the scaffolding may be on the graft's blood flow contacting, or interior, surface. As depicted in FIG. 1, after a self-expanding stent graft 100 is deployed from a delivery catheter (not shown), the scaffolding expands to fill the lumen and exerts radial force against the lumen wall 105. This radial force is generally sufficient to keep the stent graft 100 from migrating and possibly causing an endoleak into the aneurysmal sac 104 and 104'. However, stent migration and endoleak occur in some cases. A higher risk of endoleak occurs in vessels that have irregular shapes or are shaped such that they exacerbate hemodynamic forces within the lumen. Stent graft migration often results in the aneurysmal sac being exposed to blood pressure again, and some surgeons believe that endoleaks increase the risk of aneurysm expansion or rupture above that which existed before placement of the stent graft. Therefore, it would be desirable to have devices, compositions and methods that minimize post implantation stent graft migration and endoleak.

Endothelialization around a stent or stent graft is one process that can reduce the risk of stent or stent graft migration. While natural endothelialization around a stent or stent graft has been observed to spontaneously occur in some patients within weeks of implantation, this natural endothelialization is not complete or consistent. Thus, the administration of endothelialization factors before, during or relatively soon after stent graft implantation can more completely and consistently induce endothelialization around stent graft, and, as a result, can decrease the risk of migration, improving clinical outcome after stent grafting. Appropriate endothelialization factors include, without limitation, vascular endothelial growth factor (VEGF) and fibroblast growth factors 1 and 2 (FGF-1, FGF-2), however, those of skill in the art will recognize that numerous other growth factors have the potential to induce cell-specific endothelialization.

The methods and devices according to the present invention provide mechanisms to deliver bioactive materials to a treatment site while maintaining nearly-constant pressure at the treatment site. One example of an injection catheter is depicted in FIGS. 2A and 2B. FIG. 2A depicts a side cross-sectional view of one injection catheter that has one injection lumen 205 and one exit lumen 207. Associated with these lumens is an injection port 209 and an exit port 211, respectively. FIG. 2B depicts a side view of the same embodiment depicted in FIG. 2A and shows injection and exit ports 209 and 211. Inclusion of an exit port 211 and exit lumen 207 in addition to an injection port 209 and injection lumen 205 provides a mechanism for excess fluid in the space to exit the space as bioactive materials are introduced. This exit of excess fluids allows the maintenance of a nearly-constant pressure as bioactive materials are introduced at a treatment site. This maintenance of nearly-constant pressure decreases the risk that the introduction of bioactive materials at a treatment site would lead to vessel rupture.

While the embodiment of the injection catheter depicted in FIGS. 2A and 2B has one injection lumen and one exit lumen. Injection catheters can have two injection lumens and one exit lumen; one injection lumen and two exit lumens; two injection lumens and two exit lumens, (using one lumen as a manifold or supply separate lumens for each so designated opening) etc. In embodiments including more injection lumens than exit lumens, however, practitioners must be careful to not introduce bioactive materials to a treatment site more quickly than excess fluids can exit through exit lumens. One non-limiting way that practitioners can avoid introducing bioactive materials too quickly when there are more injection ports than exit ports is to introduce bioactive materials sequentially through the more than one injection ports rather than concurrently. In another embodiment of the injection catheters of the present invention this risk can be alleviated by including exit ports and lumens with a larger diameter than the injection ports and lumens.

In the embodiments of the injection catheter depicted in FIGS. 2A and 2B, the injection port 209 is distal on the length of the injection catheter to the exit port 211. Other embodiments can include exit ports that are distal to the injection ports along the length of the injection catheter from a common feed or collection lumen, or in rare cases from separate feed and collection lumens. Injection ports and exit ports can also be interspersed along the length of the catheter. A treating physician can choose the most appropriate configuration for a particular stent or stent graft deployment based on a number of factors, including, without limitation, the direction of blood flow at a particular treatment site.

Figure 3:
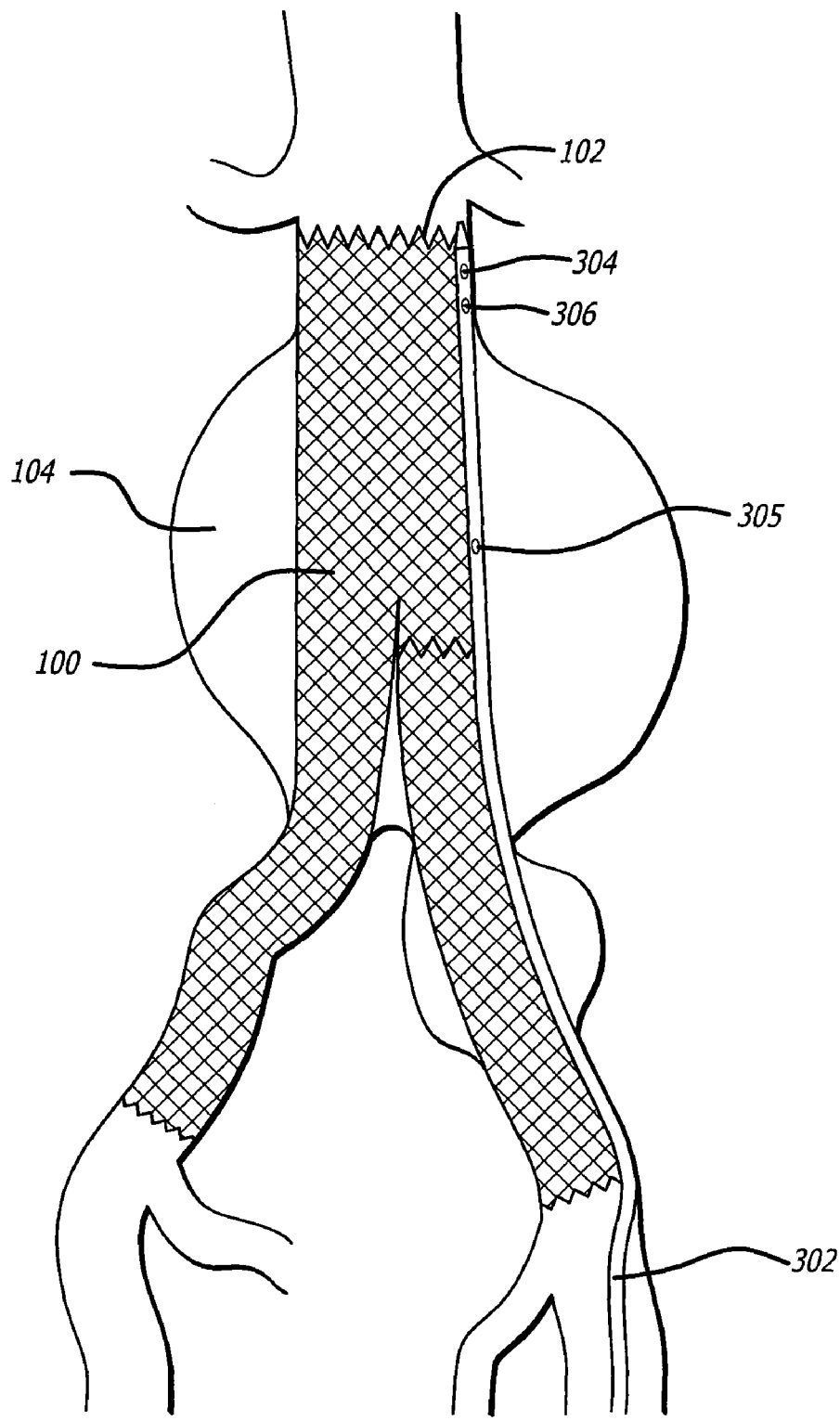
FIG. 3 depicts a deployed stent graft with an injection catheter according to the present invention at the treatment site.

FIG. 3 depicts an injection catheter 302 placed along the side of a deployed stent graft 100. The injection catheter 302 is independent of the catheter that delivered and deployed the stent graft 100. Injection ports 304 and 306 are positioned along a portion of the vessel where endothelialization would be advantageous near the distal end 102 of the stent graft 100. Exit port 305 is found within the aneurysmal sac 104 and can accept fluids displaced by bioactive materials introduced to the treatment site.

Figure 4A:
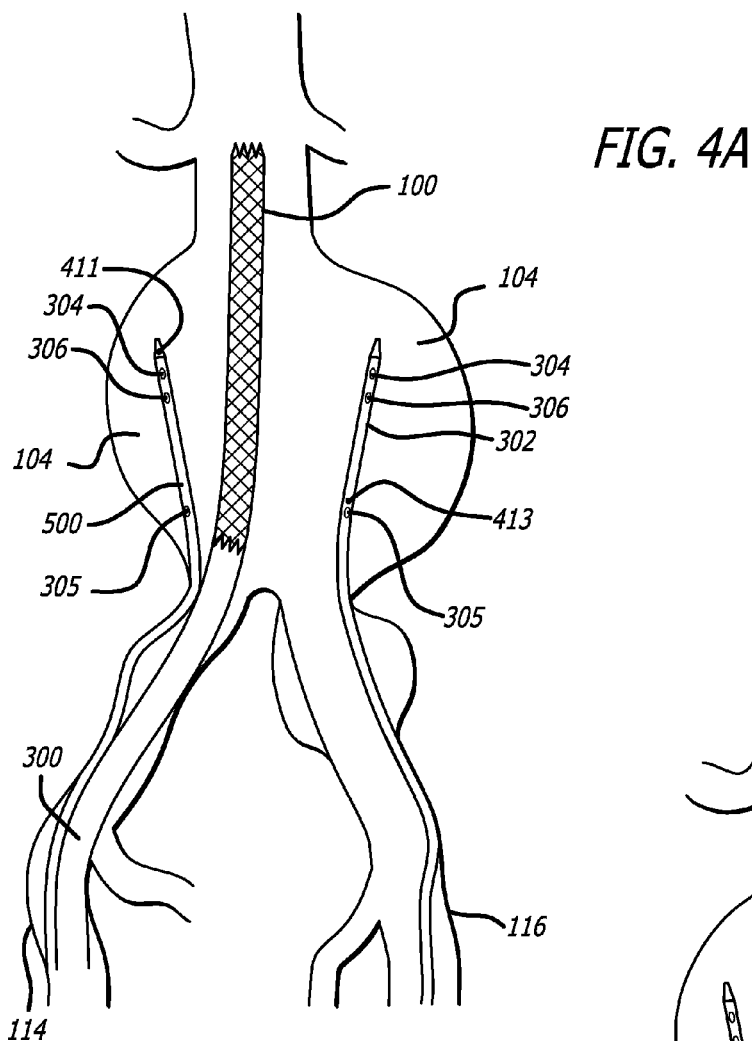
FIG. 4A depicts a delivery catheter and stent graft at a treatment site with two injection catheters before stent graft deployment.

FIG. 4A depicts injection catheters 302, 500 as they could be used in conjunction with an independent deliver catheter 300. The stent graft 100 is radially compressed into a stent graft chamber of stent delivery catheter 300. Stent delivery catheter 300 is then deployed to a treatment site via the left iliac artery 114. Multilumen injection catheters 302, 500 are also deployed to the treatment site through the right iliac artery 116 and the left iliac artery 114. The multilumen injection catheters 302, 500 can be coaxial catheters with one or two injection lumens and one or two exit lumens. If required, a guide wire lumen can also be included. Injection catheters 302, 500 have injection ports 304 and 306 through which one or more bioactive materials can be delivered to the treatment site. Exit port 305 provides an avenue for fluids in the area of the treatment site to exit before a significant increase in internal pressure in the area occurs.

In one embodiment, injection catheters 302, 500 can include sensors to continuously (or intermittently) monitor conditions at the treatment site during bioactive material delivery and/or stent graft deployment. The sensors can be found anywhere along the injection catheter that, during stent or stent graft deployment, is at or near the treatment site. In injection catheter 500, the sensor 411 is found on the distal end of the injection catheter 500. In injection catheter 302, the sensor 413 is found near the location of exit port 305. In one embodiment, the sensors that can be included are pressure sensors that can be used to monitor pressure as bioactive material(s) are introduced to the area. In other embodiments the sensors can be one or more of temperature sensors, pH sensors, blood sugar sensors, blood oxygen sensors, motion sensors, flow sensors, velocity sensors, acceleration sensors, force sensors, strain sensors, acoustic sensors, moisture sensors, osmolarity sensors, light sensors, turbidity sensors, radiation sensors, electromagnetic field sensors, chemical sensors, ionic sensors and/or enzymatic sensors.

In one embodiment, the sensors can employ wireless telemetry to deliver information from the implantation site to an instrument external to the body. In another embodiment, the sensors can be constructed in accordance with the teachings of U.S. Pat. No. 5,704,352 to Tremblay and Buckles which is incorporated by reference. Alternatively, sensors as described in U.S. Pat. No. 6,632,196 to Houser, which is incorporated by reference can also be used. Other appropriate sensors include, without limitation, optical-fiber based transducers as manufactured by RJC Enterprises of Woodinville, Wash. and described in U.S. Pat. No. 6,052,613 to Takaki or as described in "Fiber-optic Transducer Aids Heart Monitoring," Engineering News, Jun. 7, 1999, both of which are incorporated herein by reference. A model FOP-M in-vivo pressure sensor, manufactured by FISO Technologies, of Quebec, Canada, also can be used as well as other sensor constructions that are known to those of ordinary skill in the art.

Figure 4B:
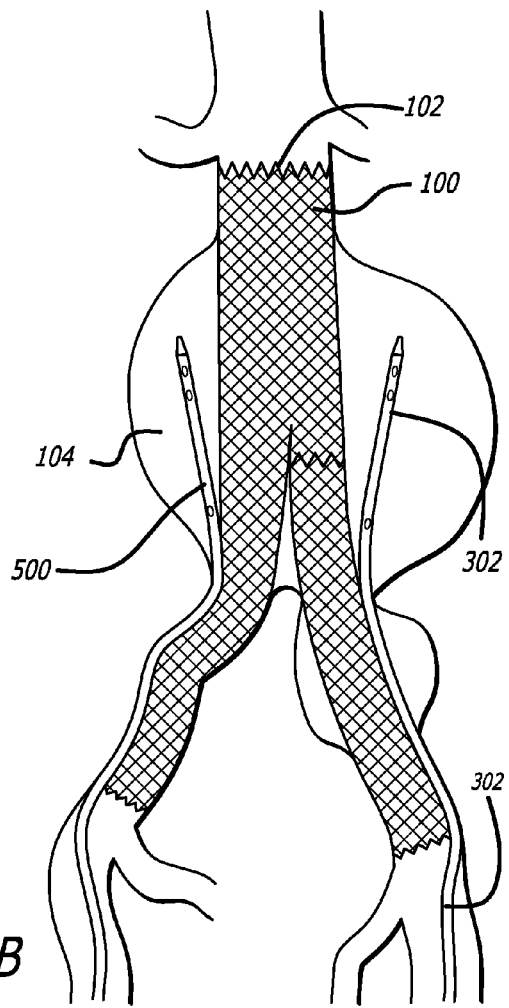
FIG. 4B depicts the same treatment site once the stent graft has been deployed and the delivery catheter removed.

In the first step of the deployment scheme depicted in FIG. 4A, the stent delivery catheter 300 and the injection catheters 302, 500 are deployed independently to the treatment site. As shown in FIG. 4B, the injection catheters 302, 500 can remain in the treatment site after stent graft 100 deployment and removal of the delivery catheter. Here, the injection ports are not aligned with the distal end 102 of the stent graft 100, but instead are found within the aneurysmal sac 104. Bioactive materials can be injected simultaneously or sequentially between the two injection catheters 302, 500. The injection catheters 302, 500 can then be retrieved. This same procedure can be repeated as necessary to apply bioactive materials to the stent graft and/or luminal wall and/or at other locations as needed. In one embodiment, thrombin and platelet-rich plasma (PRP) can be injected simultaneously to form autologous platelet gel (APG). An amount of PRP and thrombin necessary to produce enough APG to fill the aneurysm sac and seal the ends is determined radiographically by measuring the size of the aneurysm sac prior to surgery. The injection catheters are then retrieved.

Figure 5A:
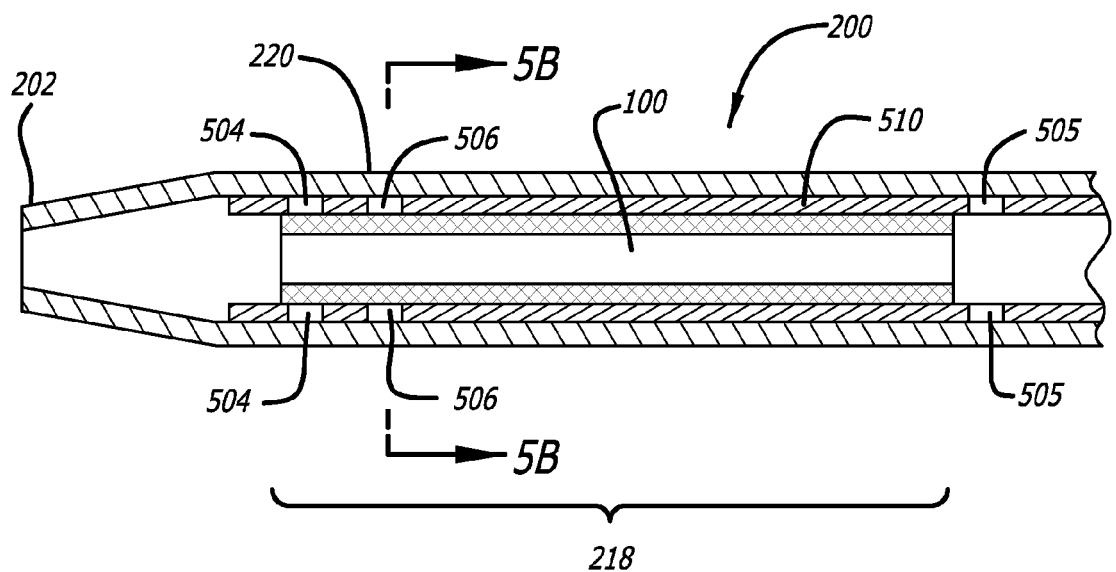
FIGS. 5A and 5B depict side and cross sectional views of a catheter system including a delivery catheter that includes a stent or stent graft and an injection catheter.
Figure 5B:
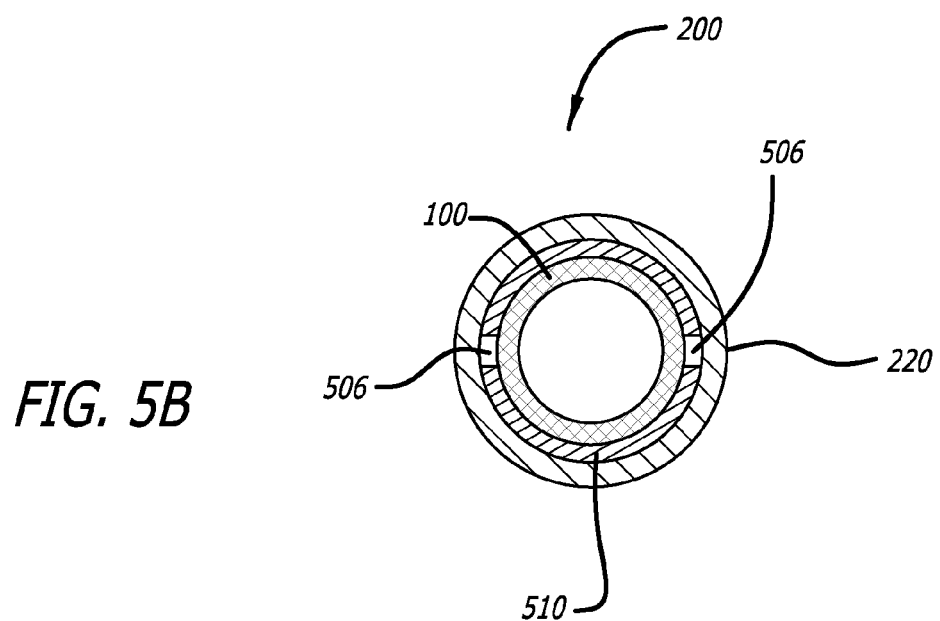

Previously-described injection catheters are independent of delivery catheters. In one embodiment, the injection catheters can be part of a delivery catheter system. This type of system is depicted in FIGS. 5A and 5B. As shown in FIG. 5A, a stent graft 100 can be pre-loaded into the distal end 202 of a delivery catheter 200. Stent graft 100 is radially compressed to fill the stent graft chamber 218 in the distal end 202 of catheter 200. The stent graft 100 is covered with a retractable sheath 220. Between the stent graft 100 and the retractable sheath 220 is a multilumen injection catheter 510 (see FIG. 5A and FIG. 5B for a cross-sectional view of 5A). In the embodiment depicted in FIG. 5A, injection catheter 510 includes two injection ports 504 and 506 and an exit port 505. Injection catheter 510 can also have a guide wire lumen. With the described delivery catheter, bioactive materials can be delivered contemporaneously with stent graft deployment.

The terms "a" and "an" and "the" and similar referents used in the context of describing embodiments are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate embodiments according to the invention and does not pose a limitation on the scope of the invention otherwise claimed.

Groupings of alternative elements or embodiments according to the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Embodiments according to this invention are described herein. Of course, variations on those embodiments will become apparent to those of ordinary skill in the art upon reading the foregoing description. The inventor expects skilled artisans to employ such variations as appropriate, including variations other than specifically described herein.

Furthermore, numerous references have been made to patents and printed publications throughout this specification. Each of the above cited references and printed publications are herein individually incorporated by reference in their entirety.

In closing, it is to be understood that the embodiments according to the invention disclosed herein are illustrative, but do not limit, alternative configurations which may be utilized in accordance with the teachings herein.

What is claimed is:

1. An injection catheter comprising:
    a proximal end, a distal end, at least one injection lumen and at least one exit lumen,
    wherein said injection lumen comprises an injection port adapted to deliver bioactive material(s) to a treatment site,
    wherein said exit lumen comprises an exit port adapted to receive and transport fluids accumulating at said treatment site that would otherwise contribute to an increased volume and pressure in the area caused by the injection of said bioactive materials and wherein said fluids exit said treatment site through said exit port and said exit lumen into said catheter and are removed from said treatment site, wherein said injection catheter maintains a near-constant pressure at said treatment site;
    wherein said injection catheter is part of a system comprising a delivery catheter and a stent or stent graft, wherein said delivery catheter comprises a retractable sheath and said injection catheter, wherein when said stent or stent graft is loaded into said delivery catheter, a portion of said injection catheter containing said injection port is disposed between said retractable sheath and said stent or stent graft.

2. The injection catheter according to claim 1, further comprising a sensor.

3. The injection catheter according to claim 2, wherein said sensor is a pressure sensor.

4. The injection catheter according to claim 1, wherein along the length of said injection catheter, said exit ports are proximal to said injection ports.

5. The injection catheter according to claim 1, wherein along the length of said injection catheter, said injection ports are proximal to said exit ports.

6. The injection catheter according to claim 1, wherein said injection catheter comprises two injection lumens, two injection ports at the distal ends of said two injection lumens, two exit lumens and two exit ports at the distal ends of said exit lumens.

7. The injection catheter according to claim 6, wherein along the length of said injection catheter the positioning of said injection ports and said exit ports is selected from the group consisting of said exit ports being proximal to said injection ports, said injection ports being proximal to said exit ports and said injection ports and said exit ports being interspersed.

8. The injection catheter according to claim 1, further comprising a guide wire lumen.

* * * * *